United States Patent
Hauser et al.

(10) Patent No.: US 8,337,901 B2
(45) Date of Patent: Dec. 25, 2012

(54) PROCESS FOR THE MANUFACTURE OF CELLULOSE SULFATE WITH IMPROVED CHARACTERISTICS

(75) Inventors: Oliver Hauser, Vienna (AT); Steffen Fischer, Freital (DE); Kay Hettrich, Schwielowsee (DE); Wolfgang Wagenknecht, Teltow (DE)

(73) Assignees: Ziel Biopharma Ltd., Limerick (IE); Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 1017 days.

(21) Appl. No.: 11/908,260

(22) PCT Filed: Mar. 10, 2006

(86) PCT No.: PCT/EP2006/060626
§ 371 (c)(1),
(2), (4) Date: Sep. 9, 2008

(87) PCT Pub. No.: WO2006/095021
PCT Pub. Date: Sep. 14, 2006

(65) Prior Publication Data
US 2009/0011033 A1    Jan. 8, 2009

(30) Foreign Application Priority Data
Mar. 11, 2005   (DE) .................. 10 2005 011 367

(51) Int. Cl.
*A61K 9/50* (2006.01)
*C08B 1/00* (2006.01)
*A61P 43/00* (2006.01)

(52) U.S. Cl. ........................... 424/494; 536/56
(58) Field of Classification Search .............. None
See application file for complete search history.

(56) References Cited

U.S. PATENT DOCUMENTS

| | | | |
|---|---|---|---|
| 3,507,855 A | 4/1970 | Whistler | |
| 3,528,963 A | 9/1970 | Reid | |
| 4,005,251 A | 1/1977 | Tunc et al. | |
| 4,419,316 A * | 12/1983 | Schweiger | 264/184 |
| 4,480,091 A * | 10/1984 | Brewer | 536/59 |
| 5,378,828 A * | 1/1995 | Usher et al. | 536/59 |
| 5,521,303 A | 5/1996 | Lange, III et al. | |
| 2003/0106163 A1* | 6/2003 | Neogi et al. | 8/116.1 |

FOREIGN PATENT DOCUMENTS

| | | |
|---|---|---|
| DE | 4021049 A1 | 6/1990 |
| DE | 4435082 C1 | 9/1994 |
| DE | 4435180 C1 | 9/1994 |

OTHER PUBLICATIONS

Dautzenberg et al., "Encapsulation by polyelectrolyte complex formation—a way to make hepatocyte cultures safe, efficient and on-line available", 1996, Progress Biotechnol, 11:181-188.*
Klemm et al., "New approaches to advanced polymers by selective cellulose functionalization", 1997, Acta Polymer, 48: 277-297.*
PCT Search Report dated May 29, 2006 (PCT/EP06/060626) (2 pgs.).

* cited by examiner

*Primary Examiner* — Robert A Wax
*Assistant Examiner* — Randeep Singh
(74) *Attorney, Agent, or Firm* — Hiscock & Barclay, LLP

(57) ABSTRACT

The invention refers to a method for the production of cellulose sulfate which is completely water-soluble and has an adjustable solution viscosity in aqueous solution, which qualifies the produced sodium cellulose sulfate (SCS) as auxiliary material with ideal biological compatibility for biological and medical applications, in particular it is suitable for the encapsulation and immobilization of biological objects, e.g. tissue, cells, microorganisms, enzymes or viruses in microcapsule.

24 Claims, 4 Drawing Sheets

Figure 1:
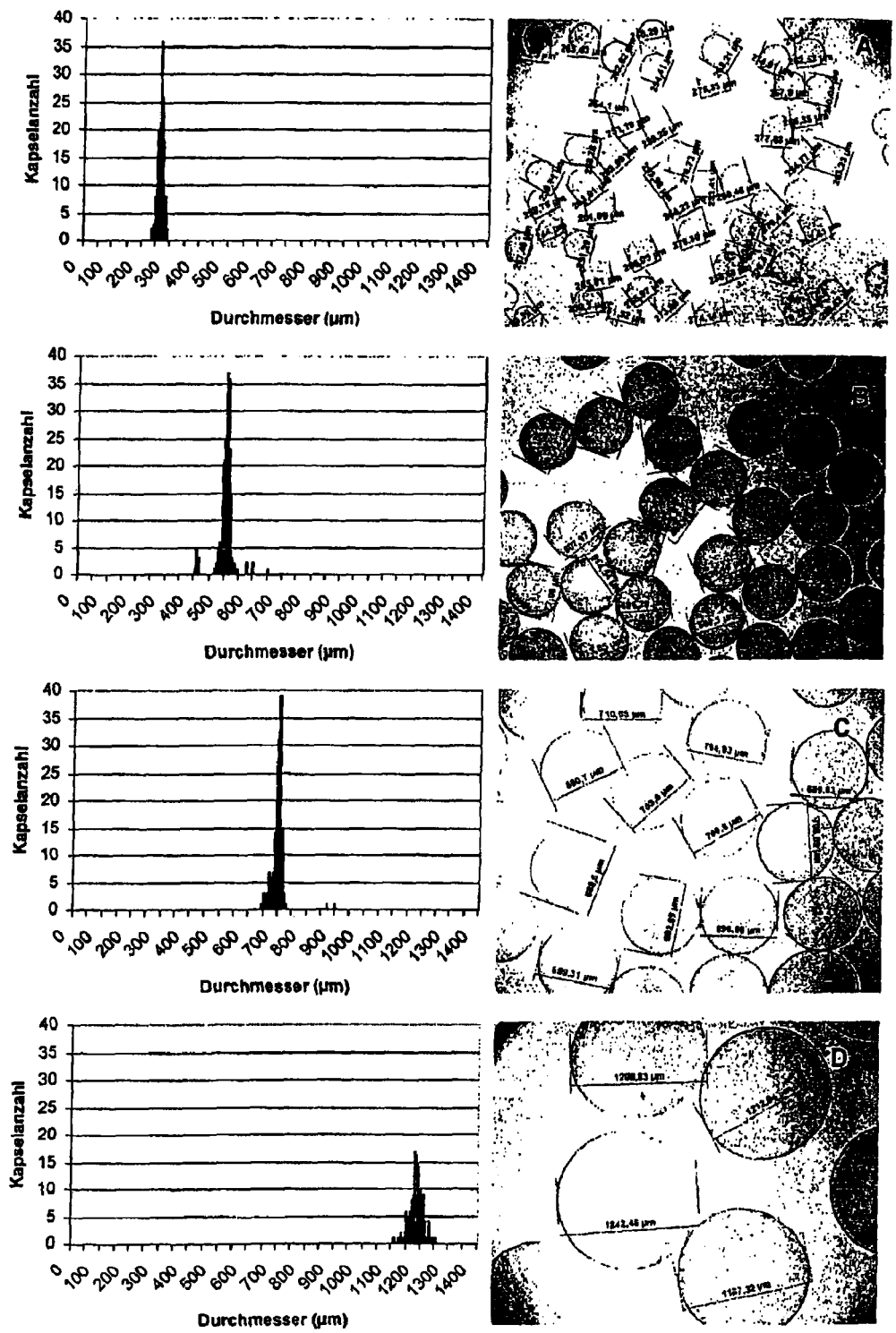

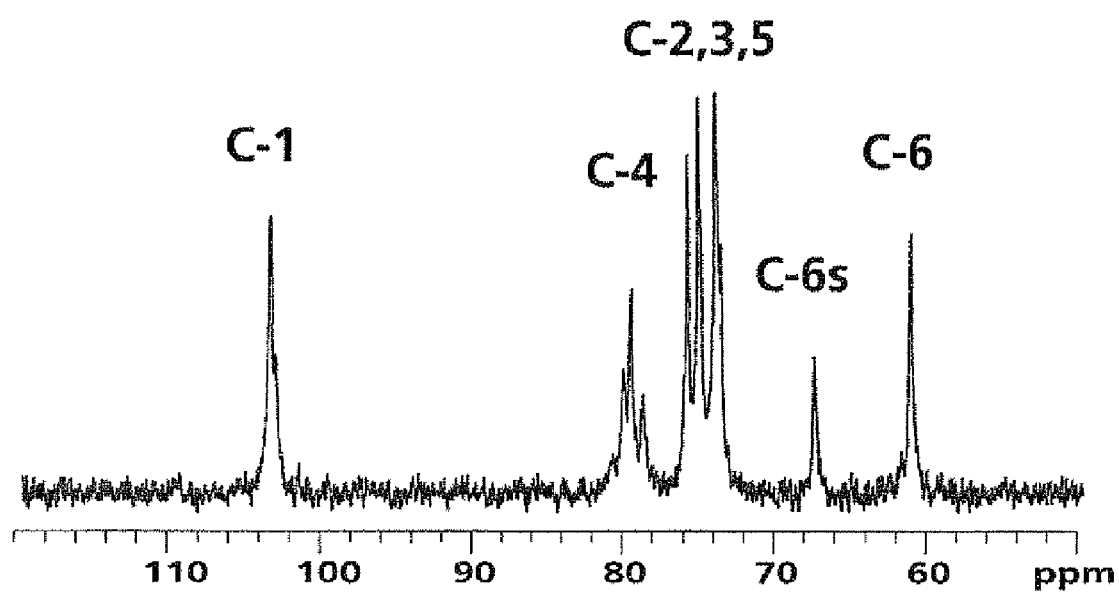
Fig 4: $^{13}$C-NMR-Spektrum of sodium cellulose sulfate (Example 1.b1 and 1.b2)

PROCESS FOR THE MANUFACTURE OF CELLULOSE SULFATE WITH IMPROVED CHARACTERISTICS

This application claims priority to and the benefit of PCT/EP06/60626, filed Mar. 10, 2006 which claims priority to German patent application DE 10 2005 011367.2, filed Mar. 11, 2005.

The invention pertains to a process for the manufacture of regio-selective substituted sodium cellulose sulfate (SCS) with improved characteristics, as well as, application of this improved SCS for the micro-encapsulation of biologically active substances. These kinds of microcapsules, also known as symplex microcapsules, are made by dribbling an aqueous solution of the improved cellulose sulfate into an aqueous solution of a polycation, preferably pDADMAC (poly(diallyldimethyl ammonium chloride)) or analogs.

Sodium cellulose sulfate (SCS) is a long known, water-soluble polymer of the sulfuric acid half ester of cellulose. SCS is formed by the esterification of the hydroxyl groups of the cellulose with a sulfating agent, e.g. sulfuric acid anhydride, sulfuric acid or their derivatives followed by the conversion of the acidified half ester into a neutral sodium salt.

Basic methods are known for the production of SCS, during which the sulfation can be carried out in a heterogeneous phase without dissolving the polymer (heterogeneous) or in a homogeneous phase either along with dissolution of the polymer (quasi homogeneous) or after prior dissolution of the polymer (homogeneous).

Lukanoff, B. and Dautzenberg, H. (1994, Das Papier, Heft 6, 287-298) further refined a well known heterogeneous method for the manufacture (U.S. Pat. Nos. 2,539,451; 2,969,355) by using sulfuric acid and propanol as reaction medium and sulfating agent. For this type of a heterogeneous method of manufacture, as per Bohlmann et al. (2002, Chemie Ingenieur Technik, 74, 359-363) the reactions medium is first prepared from 96% sulfuric acid and isopropanol in a molar ratio of 1.8:1. The sulfation of the cellulose is carried out in this at $-5°$ C. over a time period of 150 minutes. To abort the reaction the reaction mixture is removed from the cellulose sulfuric acid half ester with alcohol and washed out. Finally, the washed product is transferred into sodium salt by using sodium hydroxide.

Fundamental drawbacks of this heterogeneous method of sulfation of cellulose lie in the fact that there is a difficult to control, exothermic reaction, which inevitably leads to irregularities in the distribution of substituents along and among the polymer chain and so affects the solubility and level of polymerization of the cellulose sulfate obtained. Another aggravating drawback of this heterogeneous method of manufacture must be seen in the quick and efficient degradation of the cellulose chain during the preceding sulfation. In order to reduce the cellulose degradation washing steps, which removes adequately heat and thus prevent a further rise in temperature, finish the sulfation reaction. However, diffusion process and source process, as well as the morphological structure of the cellulose have a considerable influence on the course of the reaction, because the reaction occurs with an overall maintenance of the fixed physical structure of the cellulose.

In order to obtain complete water solubility of the heterogeneously manufactured cellulose sulfate without separation of insoluble portion in the degree of substitution (DS)-range <0.8, a pre-activation of the cellulose is recommended in DD 295858 A5 and DE 4019116 A1, whereby only the products with very low viscosity with maximum 8.5 mPas in 1% aqueous solution are obtained. During the insertion of this cellulose sulfate for the production of symplex microcapsules it must be noted, that only microcapsules with a very narrow mechanical firmness are formed.

According to DE 4021049 the cellulose sulfate with high viscosity can be isolated from the reaction products that are generated, while through additional steps in the process the water-insoluble parts can be separated and the soluble parts contained with a very low viscosity can be washed out (see Lukanoff, B. und Dautzenberg, H.: 1994, Das Papier, Heft 6, 287-298).

As a result the heterogeneous production method, by converting the cellulose into a completely water-soluble one, leads to products with relatively high substitution rates (minimum DS=0.7), and consequently an inhomogeneous substituent distribution and despite usage of high molecular starting cellulose with low viscosity.

The homogeneous sulfation of the cellulose usually leads to the formation of organically soluble cellulose intermediate, through which the degradation of the chain of the cellulose can be suppressed in an acceptable range during the sulfation reaction. As the sulfation is carried out after or simultaneously with the complete dissolution of the solid phase structure in a dipolar aprotic solvent an equable exchange of substituents takes place. The end product has a higher solution viscosity and is already in part completely water-soluble with DS-value of 0.25. As an example, using cellulose acetate with a relatively low DP (Cuoxam-DP approx. 250, DS=2.4) the viscosity of the solution of the synthesized SCS is achieved in the range of 10 mPas (measurement of a 2% solution in 2N NaOH in an Ubbelohde viscometer) (see DE 4435180).

Through further modifications of the manufacturing process based on the homogeneous esterification of the partly substituted cellulose acetates a regio-selective substitution of the OH-groups on the various C-atoms of the anhydroglucose unit of the cellulose can be achieved. Wagenknecht et al. (DE 4435082; DE 4435180 and Das Papier, 1996, 712-720) described the regio-selective sulfation on the C2/C3 or C6 position, whereby organically soluble cellulose acetate is used as the starting polymer.

Fundamental drawbacks are the low degree of polymerization of the set in commercially available cellulose acetate (Cuoxam-DP approx 200 to 350), so that after the current status of the technique no cellulose acetate can produce a cellulose sulfate with a solution viscosity higher than approx 10 mPas in a 1% aqueous solution. The modulation of a desired solution viscosity range of the obtained SCS from the given starting-DP of the cellulose acetate is still desirable.

The aceto-sulfation of native cellulose as a basic principle for the production of cellulose acetate sulfate, cellulose acetate or cellulose sulfate through mixed esterification is known since long. Thus sulfuric acid is introduced as reagent with acetic acid anhydride in a glacial acetic acid as reactions medium (U.S. Pat. Nos. 2,683,143; 2,969,356; 3,086,007; 3,075,963; 4,005,251). Instead of sulfuric acid sodium chlorosulfonate can also be used (U.S. Pat. No. 2,969,355). As a result of the testing by Chauvelon (Chauvelon, G. et al., Carbohydrate Research 338 (2003) 743-750) for the production of water-soluble cellulose acetate sulfate a strong inconsistency of this heterogeneous reaction is visible, so that the final product can be obtained only by fractioning.

Furthermore it is known that an aceto-sulfation of cellulose is possible under dissolution of the formed cellulose acetate sulfate ester by using N,N-dimethylformamide as a reactions medium. In this case acetic anhydride/sulfur trioxide (Wagenknecht, W. et al., "Cellulosics: materials for selective separations and other technologies", Kennedy, Phillips, Williams, Horwood (1993) 205-211) or acetic anhydride/chlorosulfonic acid (Wagenknecht, W., Das Papier 50 (1996) 12, 712-720) can be used as a reaction mixture. DS-sulfate up to approx. 0.8 exclusively in C6-position in the anhydroglucose unit substituted water-soluble cellulose sulfate is obtained after alkaline elimination of the unstable acetyl groups.

The drawbacks of the cellulose sulfate synthesized according to this method are in the asymmetry of the distribution of the substitution by DS<0.6, which leads to the heterogeneity in an aqueous solution and thus to the uselessness for the production of symplex membranes.

SCS as polyanion, which should fulfill the needs according to the invention for the automated production of spherical symplex microcapsules of a defined size, sufficient mechanical firmness and long-term stability, must meet a list of requirements:

Solubility in aqueous medium without leaving a residue
Adjustable solution viscosity with given concentration
Low structure viscosity, in order to maintain the regular microcapsule even in the case of high dripping velocity
Adjustable sulfate-DS in the range of 0.3 to 0.7 for stable symplex formation
Regio-selective sulfation in C6-position
Possibility to sterilize the aqueous solution at a pH-value of 7
Bio-compatibility, e.g. sterile and free of endotoxins, low heavy-metal content The biggest drawback of heterogeneous as well as homogeneous manufacturing process is the uncontrolled degradation of the length of the chain during the sulfation reaction. As a result of this degradation of the length of the chain it has not been possible, till now, to produce SCS, which is completely water-soluble in a DS of 0.3 to close to 1, preferable 0.3 to 0.6, and whose solution viscosity in a 1% solution lies in a small range i.e. of 15 to 60 mPas over the course of the aceto-sulfation reaction.

A sufficiently high, adjustable solution viscosity of the dissolved SCS is especially interesting when SCS is used to encapsulate biologically active material, then in the process used for this, a suspension of the biologically active material in an aqueous SCS-solution dropped from a nozzle into a counter-ionic solution. Be drop formation, drop homogeneity and the reproducibility of the size of the drops are directly dependent on the solution viscosity of the dissolved SCS. On the other hand, the thickness and firmness of the walls of the capsule are influenced by the degree of polymerization and the concentration of the SCS.

Though a very low solution viscosity allows the drop formation and thus a potential encapsulation of the biological material, it also leads to irregularities in the mentioned drop formation and the microcapsules arising from it. These kinds of irregularities are visible in the missing homogeneity, unequal distribution of size, lack of stability and irregular enclosure of biological materials. A very low solution viscosity of the SCS dissolved in water is thus an aggravating drawback of the conventionally produced SCS and all the products generated from it.

This drawback, namely the very low solution viscosity, is partly caused by the limitation of various manufacturing processes to use a particular cellulose raw material. The commonly used, commercially available cellulose acetate (cellulose-2,5-acetate) has an average of 250-270 polymer units (DP). Only from this DP-limit no high viscosity SCS can be obtained. During the production of SCS, especially during the sulfation with strongly acidic reagents, it leads to a further degradation of the chain, through which the solution viscosity is further reduced. Typically solution viscosity of under 10 mPas is attained (see e.g. DE 4435180).

Wood pulp, which is sometimes used as raw material, has DP-values of around 600. The use of wood pulp in the well-known manufacturing processes described above leads to distinct degradation of the chain and corresponding to that to an end product with a very low solution viscosity.

Ideally one would transform native high molecular cellulose such as cotton-linters, which has high DP-values of about 1250-1400 polymer units, into SCS, in order to get the longest possible polymer chains and thus a high solution viscosity.

Cotton linters are used as raw material in the heterogeneous sulfuric acid/propanol method, however this method of manufacture, as already mentioned, leads to a considerably number of chain ruptures, so that the products resulting after the synthesis display only a low solution viscosity. As the heterogeneous manufacturing process also does not allow even distribution of sulfate groups, the product characteristics, e.g. the water solubility of SCS, are negatively influenced.

It is thus the object of this invention to provide an additional and improved manufacturing process for regio-selective substituted SCS, which avoids the drawbacks of the state of the art and which allows the desired adjustment of the solution viscosity with complete water solubility of the end product, with the given DP of the cellulose raw material used.

The object is tackled through the process steps of the main claim 1. Exceptional embodiments are described in the features of the dependent claims.

For this method, the cellulose, preferably cotton linters, is dissolved by a quasi-homogeneous reaction in a polar solvent by mixed esterification with a mixture of reagents, consisting of an acetylating agent and a sulfating agent into an acetate-sulfate-mixed-ester. As an advantage the cellulose is first allowed to swell in the reaction medium at increased temperatures, preferably in the range of 30 to 100° C., over a long time frame, preferable 0.5 to 12 h, under sustained stirring and left to stand at room temperature for further swelling. Finally, under sustained stirring, the previously prepared reagent mixture, preferably containing an acetylating agent, a sulfating agent and a polar solvent of defined composition is added in. The partial substitution level of DS-sulfate and DS-acetate can be adjusted in a way known to a person skilled in the art up to a maximum of a total DS=3 using the molar relation of the reagents with one another and the molar relation to cellulose. The aceto-sulfation reaction takes place, preferably, in a temperature range of 30 to 80° C., whereby the cellulose acetate sulfate that is produced dissolves itself in the reaction system into a viscous solution. If the temperature is maintained predominantly constant predetermined level, the viscosity of the polymer solution decreases as the reaction goes on, so that this viscosity can be adjusted at a predetermined level.

In accordance with the invention it is important that the further degradation is stopped, by defined neutralization, and thereby fixing the level of polymerization and the viscosity of the solution of cellulose sulfate that is obtained after reprocessing.

For neutralization the sulfate half ester groups are transformed without elimination of the acetyl groups prior or alternatively, also simultaneously to the precipitation in its sodium salt form. Under the conditions in accordance with the invention, in addition to this, the sulfate half ester groups are carefully neutralized, without decomposition of the acetyl groups at any rate, prior to or alternatively also simultaneously to the precipitation with a basic neutralizer, preferably NaOH, dissolved in an appropriate neutralizer and/or precipitator.

Subsequently the cellulose sulfate mixed ester, which has preferably been precipitated in a particular form, is washed with an appropriate wash medium, preferably with ethanol containing sodium acetate or a mixture of ethanol and water.

The reprocessing for the end product is then carried out through alkaline hydrolysis of the acetyl groups in a heterogeneous phase with the help of ethanolic NaOH, back neutralization to a pH value close to 7, repeated washings preferably with aqueous ethanol till salt free and subsequent drying of the sodium cellulose sulfate in vacuum at approx 40° C.

After this process of synthesis residue free, clearly-soluble sodium cellulose sulfate can be produced with DS above or equal 0.3, which shows a very advantageous, uniform and regio-selective exchange of substituents of the sulfate half ester groups in C6-position and are identified by an adjustable solution viscosity in a range of 10 mPas to 500 mPas, preferably 15 to 400 mPas, further preferably 20 to 300 mPas, further preferably 15 to 100 mPas, further preferably 20 to 60 mPas with a given concentration of 1% in water.

As the products obtained are substantially pure, it is not necessary to further purify them by dialysis or ultracentrifugation.

Whereas in the methods known so far the neutralization was carried out at the end following the washing step and/or deacetylation, the inventors show, that when the neutralization is carried out directly at the end in the sulfation step and without prior deacetylation or washing steps, the quality of the SCS produced is clearly better. Satisfactorily good results can also be attained when the neutralization is carried out at the same time as the precipitation.

For the neutralization, in accordance with the invention of the process a base or an alkaline solution, preferably NaOH is added to the reaction mixture whereby the base, alkaline solution or NaOH is exactly coordinated with the sulfating reagent. For example 1 Mol of a tri-basic acid, such as chlorosulfonic acid is neutralized with 3 Mol of NaOH and 1 Mol of a di-basic acid, such as sulfinic acid, is neutralized with 2 Mol of NaOH.

Speedy work is advantageous during neutralization, as polymer chains are always attacked and degraded in acidic mediums, and thus the shortening of the time span during neutralization reduces such a degradation of the length of the polymer chain.

With the adjustment in the process steps concerning the manufacturing process of SCS in accordance with the invention and the early neutralization in acid system, the manufacturing process can be controlled with respect to the degradation of the length of the polymer chain. The SCS generated in accordance with the invention possesses none or only a very low structural viscosity in a 1% aqueous solution at 25° C. and is at the same time adjustable in the ranges of solution viscosity from 10 to 500 mPas, further preferably from 15 to 400 mPas, further preferably 20 to 300 mPas, further preferably 15 to 100 mPas, further preferably 20 to 60 mPas, measured in a 1% aqueous solution at 25° C.

Furthermore the SCS created in accordance with the process of the invention is water-soluble without leaving a residue and has a DS-value starting from 0.25 as against that produced by heterogeneous process using the $H_2SO_4$/isopropanol reaction, so that no water insoluble components must be removed with an additional treatment.

In accordance with the method of the invention it is possible to use as starting material celluloses of different origin and with various DS values. Preferably high molecular cellulose, especially ultra pure and substantially heavy metal free cotton linters can be used. Thereby, the grade of polymerization is limiting the adjustable ranges of viscosity.

As an option in accordance with the invention for the manufacturing process the cellulose is swelled in a polar solvent like e.g. N,N-dimethylacetamide (DMAc), N-methylpyrrolidone (NMP), dimethylsulfoxide (DMSO) or N,N-dimethylformamide (DMF). Preferably DMF is used.

In addition the process according to the invention can be carried out with the option that for the mixed esterification of cellulose acetate sulfates soluble in organic solvents and having a total DS up to 3 sulfuric acid, amidosulfuric acid, sulfur trioxide, sulfinyl chloride or chlorosulfonic acid is used as the sulfating agent. Preferably chlorosulfonic acid is used as the sulfating agent.

The process according to the invention can be carried out with the option that for the mixed esterification of cellulose acetate sulfates, which is soluble in organic solvents and has a total DS up to 3, combined with acetyl chloride or acetic anhydride is used as the acetylating agent. Preferably acetic anhydride is used as the acetylating agent.

The production of SCS in accordance with the invention should preferably take place under the conditions described below:

At first the native cellulose is swelled at a risen temperature of up to 150° C., preferably 30 to 100° C., further preferably 40 to 80° C. for up to 24 h, preferably for up to 12 h, further preferably for 3 to 8 h and as a subsequent period at room temperature, such that a further cooling down and swelling at room temperature (RT) is carried out for up to 48 h. During the entire time of the swelling the suspension will preferably be stirred. During the further swelling at RT the stirring is no longer necessary.

Subsequently the sulfating agent and the acetylating agent are added to the swelled cellulose with constant stirring and at a reaction temperature of 0° C. up to 110° C., such as preferably 20 to 80° C., further preferably 30 to 70° C., further preferably 40 to 65° C., further preferably 50 to 60° C.

While constantly stirring the obtained cellulose acetate sulfate half ester is fully dissolved and the viscosity is slowly reduced until the desired and intended fluidity of the polymeric solution, which can be experimentally defined, is reached.

The directly subsequent neutralization is preferably carried out under constant careful stirring at room temperature (RT), whereby the polymer solution can still be warm in comparison to the reaction temperature, i.e. the reaction will, for e.g. be carried out at 50° C., and will after it has cooled down a little be added to the neutralization/precipitation bath while it is still warm. The ratio of neutralization bath/precipitation bath to the polymer solution is 3 to 10, preferably 3 to 5. As a condition the SCS that is produced in accordance with this manufacturing process is basically sterile, free of endotoxins and/or heavy metals. For this purpose the process is carried out under sterile conditions and particularly germ free conditions. Particularly the conditions and raw materials are to be chosen in such a way that no yeast, aerobic bacteria, salmonellae, *E. coli, Staphylococcus aureus, Pseudomonas aeruginosa* etc. is detectable in the final product. The endotoxin content of the end product lies within the range of 0.02 to 0.11 I.E/ml and is detected by a LAL-test in accordance with the European pharmacopoeia Ph. Eur. 4.00 Method C (turbidimetric-kinetic) with a 1% aqueous solution of SCS.

In addition attention must be paid to the fact that the raw materials used are also free of heavy metals like e.g. Cd, Pb, Hg, Fe, Ni, Ti, Mn, Zn and Cu, so that the SCS manufactured from this does not exceed the following threshold values:
Total heavy metal content without iron: $\leq 10$ ppm,
Iron content: $\leq 20$ ppm,
whereby the total heavy metal content without iron contains the sum of all thinkable heavy metals.

For this it is preferred that only materials and apparatuses are employed for the reactions, which do not emit any detectable amounts of one of the above mentioned heavy metals.

According to a further embodiment the SCS produced by this method should be regio-selectively substituted. It is preferred to have an exclusive homogeneous exchange of substituents at the C6 position or alternatively an exchange of up to 30% of the sulfate ester groups at the C2/3 position. The reagents that are used control the desired regio-selective sulfation in accordance with the state of the art methods (Wagenknecht et al., 1996).

The SCS in accordance with the invention is especially suited for use in micro encapsulation of biological materials. On the basis of its adjustable solution viscosity it is easily achievable to adjust the ranges of the viscosity from 10 to 50 mPas, 40 to 70 mPas, 60 to 100 mPas, 80 to 200 mPas, 150 to 300 mPas or 250 to 500 mPas (with measuring a 1% aqueous solution in a Ubbelohde viscometer) without essentially changing the concentration of the polymeric solution. Thus, this SCS allows an uncomplicated handling and astonishingly high rate of working speed during encapsulation of biological material.

In contrast to this it has been described very limitedly in the numerous methods for production of water soluble cellulose sulfate, those that can be used for the production of micro capsule products, those that have a considerable mechanical firmness and those that attain the biochemical requirements for a potential medical use.

Thus it has been presented in DD 218734 A4 and DE 3306259 C2 methods for the production of microcapsules, whereby the immobilization of the viable biological objects has been described. The SCS that is used is thus produced using the $N_2O_4/SO_2$/DMF method. The use of the highly toxic stick oxide is a fundamental drawback of this method, in which at first a redox process forms nitrite sulfate mixed ester, which is soluble in dimethylformamide (DMF). After isolation of the unstable cellulose nitrite ester groups the resulting toxic side-products, especially carcinogenic dimethylnitrosamine must be removed from the cellulose sulfate before it can be used with living biological objects, particularly when it is used for biomedical use. However the microcapsules that are produced according to the process of the invention, are suitable for medical use.

In DE 4021050 A1 and EP 0892852 the production of SCS is described using a heterogeneous $H_2SO_4$/propanol method. It is being attempted to use this SCS for the production of symplex microcapsules for use and to immobilize viable biological objects. Because of the degradation of the length of the chain and the irregular sulfation during the production of SCS the isolation of water insoluble parts and/or removal of highly substituted low molecular parts cannot be avoided. Microcapsules from SCS manufactured in such way are less stable and very non-homogeneously formed. They are thus not suited for medical use for example in the form of injections.

DD 298643A5 and DD 299313A5 disclose a method for manufacturing a regio-selectively, at the position C6, substituted cellulose sulfate, which was generated employing an inorganic solvents soluble trialkylsilyl cellulose, and which leads to products with a broad range of solution viscosities. It is further mentioned that these products could be used in the field of biotechnology, pharmacy and medicine. However, these potential areas of use are not supported by any experimental data. It is regarded as a serious disadvantage of this technology that it seems not to be possible to establish a desired solution viscosity although the DS is kept stable and that the solution viscosity obviously depends on the DP of the starting material and the level of sulfation (Philipp et al., Das Papier 49(1995)2, 58-64).

DE 19837673 A1, DE 19838535 A1 and WO 2000010694 A1 describe the use of the anionic ester of the sulfoalkyl cellulose as an anionic symplex component for the production of flat membranes. A production of symplex flat membranes is fundamentally different from the production of capsules. Thus no conclusions can be drawn for the use of SCS for the production of microcapsules.

Also in Richau, K. et al., J. Membr. Sci 1996, 113, 31-41 and in DD 298790 A5 it has been described that SCS with a low viscosity, which was manufactured from commercially available cellulose-2.5-acetat, can be used for the production of symplex flat membranes (Cellulose Chem. Technol. 25(1991) 343-354). The manufacture of symplex flat membranes is fundamentally different to the manufacture of capsules and conclusions cannot be drawn for the use of SCS for the production of microcapsules, especially not for the production of microcapsules useful in a biomedical area.

Wagenknecht et al. (DE 4435180 C1; Das Papier 50 (1996) 12, 712-720) describe the synthesis and use of SCS for symplex flat membranes, which is produced from cellulose acetate. The SCS is thus produced by the homogeneous sulfatation of mostly low molecular cellulose-2.5-acetate in N,N-dimethylformamide with different sulfating agents and subsequent decomposition of the acetyl groups, whereby the reprocessing is carried out salt free. The solution viscosity of the SCS produced in this way is unsatisfactorily low. Although this SCS might be useful for the manufacturing of symplex flat membranes, which can be used for a separation of solvents. Microcapsules, which are produced from SCS produced in such way, are less stable and very non-homogeneously formed. They are thus, not suited for medical use e.g. in the form of injections.

The low viscous SCS, as it is described in DE 4435180, is also qualified e.g. for the separation of solvents without distillation through pervaporation. The SCS described in DE 4435180 is manufactured by sulfating commercially available cellulose acetate and shows shortened polymer chains as well as a low solution viscosity. Microcapsules that are produced out of this kind of SCS are rarely stable and non-homogeneously formed. They are thus not suitable for medical use e.g. in the form of injections and for a reproducible release of pharmaceutical substances.

As a summary it is determined that numerous methods are known for the production of SCS, which however give all end products, which either have a very low solution viscosity, irregular distribution of substituents, consists completely or predominantly of short fibers due to numerous degradations of the chain or are polluted by the use of toxic reagents.

Also when such SCS is used, at a laboratory level, for the micro encapsulation of biological materials, the capsules prove to be unstable and as non-homogeneous in their size and thickness of the membrane. Considerable negative impacts were seen also through the toxic load caused by the manufacturing process on the viability of the enclosed cells, or rather for the biocompatibility of the capsules.

Another objective of the present invention is thus to produce from native cellulose clearly-soluble cellulose acetate sulfates with defined molecular structure, as well as to produce completely water soluble, biologically compatible SCS from it with improved solubility characteristics, which can be used as auxiliary materials for biological and medicinal use, and can especially be used for the immobilization of active biological objects in microcapsules from symplex membranes.

Unlike the previously described method of manufacture and end products the SCS produced in accordance with the invention is distinguished e.g. by a defined adjustable solution viscosity range, which can be achieved by using a starting material with adequately high degree of polymerization (DP) value and by controlling a slow degradation of chain during the homogeneous phase of the process of manufacture. The SCS, which is produced by currently described method, through these characteristics, resolves the previously described problems during micro-encapsulation of biological materials.

Basically microcapsules can be divided into three categories: solid spheres, coated spheres and hollow spheres.

Solid spheres can be produced while gelatinizing substances (e.g. agarose, gelatin) are dissipated into the fluid aggregate as drops and are cooled to below their melting point to solidify them. The matrix used for solid spheres presents a combination of e.g. alginate and calcium chloride ($CaCl_2$) or other polyvalent metal ions. Hollow spheres can be produced like solid spheres by dribbling the polymer solution into a bath with countercharged ions. The countercharged ions used should not penetrate the drops that are dipped into it on the basis of diffusion limitations. Consequently the linking reaction takes place only on the upper surface of the drop, through which a stable membrane is developed around a fluid core. Dissolving a linked core or dissolving the core of a solid sphere can also develop hollow spheres. Coated spheres can be produced from solid or hollow spheres by the deposition of one or several additional layers, of complex building substances, which are made of oppositely charged poly-ions (e.g. PLL (poly-L-lysine), Chitosan).

The SCS, which has been produced according to the invention, is qualified especially for the production of hollow spheres or coated spheres.

There are a variety of methods and corresponding technical variations known for the manufacture of microcapsules. In the simplest case simple dripping of a fluid, which flows through a cannula produces the capsules. The weight force and the product of the interfacial tension and external diameter of the cannula determine the size of the dripping drops. This procedure is applicable only for capsules larger than 1 mm but has only a limited productivity.

By the so called Air-Jet process, also Air-Stripping process, a gravimetrically ejecting fluid drop is carried to the end of a feeding concentric capillary through a laminar gas flows flowing around the capillary. Through this process the diameter of the drop can be reduced.

Through Air-Knife process the jet of ejected fluid is broken into tiny droplets by a turbulent whirl of air. Both processes however have a low productivity of approx 0.1-2 ml/min.

In contrast to Air-Jet process, in which the drop formation is carried out purely gravimetrically and is thus not suited for solutions with high viscosity, the Jet-Cutter process gives a constant flow of fluid with given pressure. The jet of fluid is dissipated mechanically using a rotating wire. Spherical particles are created from the separated fluid cylinders with interdependence on the surface tension of the fluid over a corresponding fall route. Adverse to this process is the system related slice and spray wastage.

An electrostatic supported drop formation accelerates the drop formation at the capillary through the application of a strong electric field between the capillary and the integration bath, whereby substantially small drops drip from the capillary as in the case of gravimetrically dripping.

During the process of drop formation with the help of rotating discs, a watery fluid is introduced near the mid-point of a fast rotating disc and it then flows through the centrifugal force that is created to the edge of the disc. At the edge of the disc the fluid film is ripped into small droplets. The drop formation is improved by heterodyning an oscillation on the fluid.

During the process of drop formation with a rotating cylinder, the watery fluid flows through a rotating cylinder with defined openings. The centrifugal force facilitates the drop formation at the edge of the cylinder, where the fluid is ripped into tiny droplets.

The drop formation from jets of fluids makes it possible to increase the volume flow and consequently the productivity. Here one can differentiate mainly 3 methods:

In the case of dipping stream process, a fluid stream is injected at high speeds into another fluid. Due to the high shearing force the jet is dissipated into fine droplets, however with a large variation of sizes.

In the case of vibrations process superimposing a sinusoidal oscillation with appropriate frequency dissipates a laminar jet of fluid ejecting from a nozzle. The principle is traced back to Lord Rayleigh (*Proc. London Math, Soc.* 10(4), 4-13, 1878), who had allocated a not so viscous flow of fluids, that disintegrated a fluid cylinder, when that wavelength of a rotationally symmetric oscillation increases, as does the range of the undisturbed jet. The optimal wavelength depends on the diameter, the dynamic viscosity, the density and the surface tension of the fluid.

In addition to this there are numerous other methods and modifications of the method described above. Renken and Hunkeler give an overview of this process (Renken A. and Hunkeler D., Microencapsulation: A Review of Polymers and Technologies with a Focus on Bioartificial Organs, Polimery, 43(9), 530-537 (1998)).

All these methods as described above are suitable for the production of microcapsules as stated in this invention.

Encapsulating machines (IE-50R) manufactured by the company Inotech (Dottikon, Switzerland) were used for the production of microcapsules, namely from SCS-droplets with homogeneous size distribution. These work based on the vibrations process described above. For biomedical usage all the process steps mentioned in this specification can also be carried out under sterile conditions. A description of such an encapsulating machine and the functionality can be found for e.g. in EP 1 062 032 B1.

According to Lord Rayleigh, during the encapsulating process, a watery solution of SCS is delivered from a storage container through a nozzle with the help of constant air pressure or a peristaltic pump or linear propulsion in order to generate a constant jet of fluid. In this way a constant flow of volume can be adjusted and in consequence equal sized capsules can be generated. Depending on solubility and solution viscosity, which is conditioned by the chemical characteristics of the SCS as per the invention, which is freely adjustable for a given nozzle within a broad range, a high working speed is possible. Volume flows in the range of 1-15 ml/min, preferably 6-9 ml/min can be used depending on the ejecting capillary.

Depending on the purpose, the watery solution of SCS can hold additional components in different parts. For this the encapsulated material matters first. In addition to this, additional components can be added in varying proportions (e.g. substrate, anti-freeze agent (e.g. glycerin, DMSO) proteins, solvents or salt, like e.g. 0.9% NaCl) or the SCS can directly be dissolved in special solutions (e.g. cell culture medium).

A vibration transmitter creates and transmits a vertical sine vibration onto the fluid flowing through the nozzle in a variable range from 100 to 4000 Hz. For the production of microcapsules frequencies in the range of 600 to 3000 Hz are preferably used. In addition to the frequency the amplitude of the vibration can also be varied from 0 to 100%. With this vertical vibration that is created the dissipation of the ejected jet of fluid into droplets with the same volume can be achieved. Principally with the vertical sine vibration the production of a defined capsule size can be given.

In order to impede the collision of the droplets during the flight phase a charge displacement is created in the ejected jet of fluid by applying a high voltage, in the range of 0.8 to 1.5 kV, between the nozzle and a positively charged electrode (anode). By passing a current through a voltage arm the negatively charged droplets, which are negatively polarized on the nozzle are pulled in the direction of the anode and thus directed horizontally.

The resulting anionic droplets develop at its surface a shell shaped symplex membrane surrounding a core of non-complexated fluid; the shell is formed through the complexation of the anionic poly-electrolyte contained in the droplet with the cationic poly-electrolyte (e.g. pDADMAC) contained in the complexation bath on the phase interface of the droplet. The thickness of the membrane increases with the duration it remains in the watery solution of the polymeric cation.

The complexation bath consists of a watery solution of a polymeric cation with different molecular weights. The stability of the symplex membrane that is formed is thus determined by the chemical characteristics (functional groups, number and distribution of substituents). For e.g. dodecylamine, ethylendiamine, piperazine, methylene blue, arginine, poly(allylamine hydrochloride), triethyltetramine or spermine are suitable for the encapsulating process. Preferably polymers with quaternary ammonium groups are used, more preferably salts of poly(diallyldimethyl ammonium) or poly(vinylbenzyltrimethyl ammonium), preferentially poly (diallyldimethyl ammonium chloride) (pDADMAC) or poly (vinylbenzyltrimethyl ammonium chloride).

The level of integration, namely the stability of the microcapsules created correlates further with the length of the chain of the polycation used. The average molecular weight can lie in the range of 10,000 to 500,000, preferably between 15,000 and 50,000 in the case of pDADMAC. The suitable concentration of pDADMAC for the encapsulation are in the range of 0.5-5% (w/v), preferably in the range of 0.8-2% (w/v).

The watery polycation solution can contain additional components in varying proportions depending on the purpose, e.g. substance, which reduce the surface tension of the aqueous solution, organic solvents, anti-freeze agents (glycerine, DMSO) or salt, like e.g. 0.9% NaCl or the polycation can be directly dissolved in special solutions (e.g. culture medium).

In the complexation bath there is a magnetic stirrer, which creates a vertical current towards the drop-direction of the drops and thus transports the droplets that are formed out of the region where the new drops are falling so that the risk of an aggregation of not yet completely formed microcapsules is minimized. Furthermore the stirrer holds the floating droplets, which is advantageous for the convection of the membrane building reaction and also the subsequent wash step.

For the production of microcapsules as per the invention at first an aqueous solution of SCS is to be produced. The SCS solution should have a concentration between 1% and 4% (w/v), preferably between 1.5% (w/v) and 3% (w/v). Depending on the shearing force the suitable parameters can be read off a viscosity diagram. Thus, e.g. a 1% solution of the SCS, as per the invention, should exhibit a solution viscosity in the range of 10 to 500 mPas, preferably from 10 to 200 mPas, further preferably between 15 and 80 mPas, further preferably between 20 and 50 mPas or between 40 and 60 mPas.

In accordance with an embodiment the SCS, manufactured in accordance with the invention, forms basically in spherical particles, namely microcapsules in the sense of the invention exhibiting a diameter of 0.1-50 μm, 1-100 μm, 50-250 μm, 50-500 μm, 100-250 μm, 100-500 μm, 250-500 μm, 250-700 μm, 500-1000 μm, 700-1500 μm, 1000-2500 μm, 1500-3000 μm, 2500-4000 μm, 3000-5000 μm. The microcapsules preferable exhibit a diameter of 200-1500 μm, further preferably 600-800 μm.

For biomedical usage the SCS solution, created from the SCS generated in accordance with the invention, can be sterilized by current methods, e.g. through radioactive radiation. The stability of the SCS generated in accordance with the invention proved itself during the sterilization in vapor for 30 min at 121° C.

The SCS produced in accordance with the invention is particularly suited to produce more stable and more homogeneous microcapsules. Such microcapsules are suitable to enclose biological objects e.g. bacteria, viruses, yeasts, cells and tissue for biomedical usage, but also for the production of pharmacologically active ingredients in biotechnological scale. They can also be used for the immobilization of pharmacologically active ingredients e.g. powder catalysts, colloids, metal complexes, enzymes, antibodies, dyes and pigments for technical use.

The capsules produced in accordance with the invention are thus especially suited for use in veterinarian and human medicine, because they fulfill the high requirements as explained below.

For the use of the microcapsules in the blood circulatory system or in animal or human tissue, namely organs, e.g. for treatment of cancer, it is necessary that the microcapsules are correspondingly uniform and reproducible in a variety of sizes so that on the one hand the congestion/blockage of the injection cannula and/or blood vessels can be avoided. Furthermore the application of a constant quantity of encapsulated agents per capsule (e.g. pharmacologically active ingredients, enzymes, number of cells per capsule) can be guaranteed. The spherical geometry of the capsules guarantees a good flow e.g. in catheters and an equal-in-all-directions and ideal release of the pharmacologically active ingredients. Furthermore the slight compressibility of the capsules is useful, because this reduces the chances of the capsule getting stuck and hence the blockage of the catheter e.g. by compressed capsules. A minor stickiness on the upper surface of the capsule, especially in biological fluids, prevents the agglomeration of the capsule. The SCS, which has been produced by the method described in the invention above, on the basis of the adjustable solution viscosity allows an uncomplicated handling and an unexpected high speed of work during encapsulation of biological materials, this is especially advantageous for the industrial manufacture of pharmaceutical compounds based on microcapsules.

Additional advantages and applications of the above invention have been described below on the basis of examples that have been carried out in regard to the figures:

FIG. 1 shows a microscopic measurement of the distribution of sizes of the SCS capsules with different desired sizes (FIG. 1 A-D) manufactured in different batches using the Inotech encapsulator IE-50R and a Zeiss Axiovert for determination of the capsule size distribution. In each case the SCS-solution as well as the pDADMAC solution comprised 1% NaCl (w/v). The amplitude of the oscillation of the nozzles amounted to 100% each time. The other variable parameters were adjusted as below.

TABLE 1

| FIG. | Capsule size +/ STD (µm) | SCS (%) | pDADMAC (%) | Nozzles Ø (µm) | Volume current (ml/min) | Frequency (Hz) | Voltage (V) |
|---|---|---|---|---|---|---|---|
| A | 264 +/− 10 | 1.5 | 0.85 | 100 | 1.5 | 2000 | 1300 |
| B | 521 +/− 16 | 1.8 | 1.00 | 200 | 6.1 | 1100 | 1100 |
| C | 703 +/− 38 | 2.8 | 1.50 | 250 | 8.5 | 700 | 1100 |
| D | 1180 +/− 32 | 2.0 | 2.50 | 300 | 12.9 | 600 | 1200 |

By choosing suitable parameters for the capsule production, one can get a wide range of sizes for the microcapsules that are produced. The bandwidth ranges from 10 to 5000 µm depending on the adjustable solution viscosity of the SCS produced in accordance with the inventions. The microcapsules, of all tested sizes, that are formed exhibit an almost perfectly ideal spherical geometry and a high level of reproducibility.

Figure 2A:
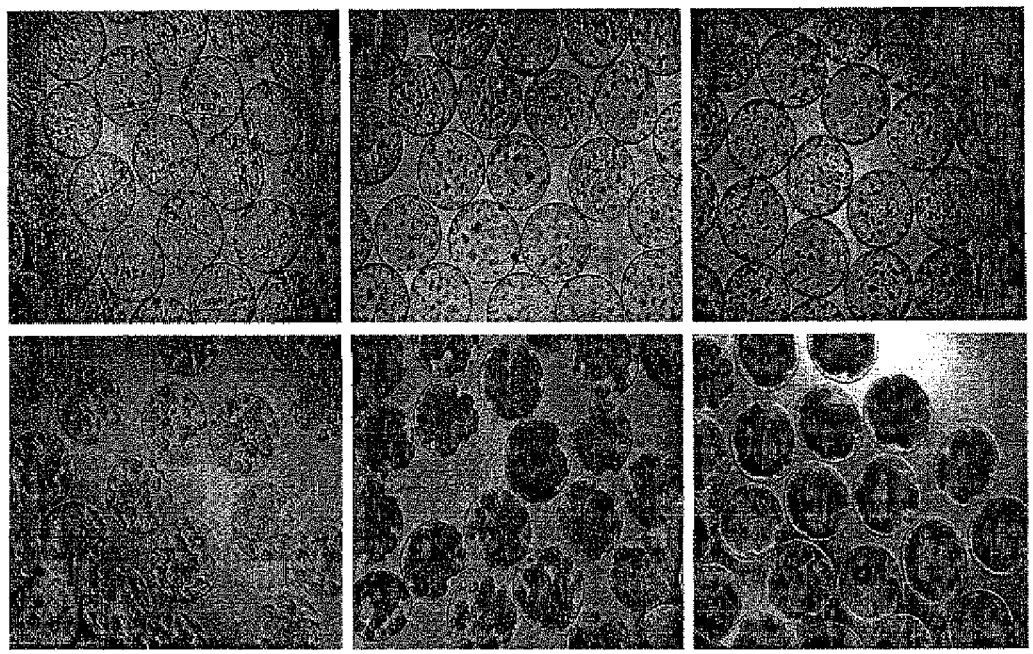
Figure 2B:
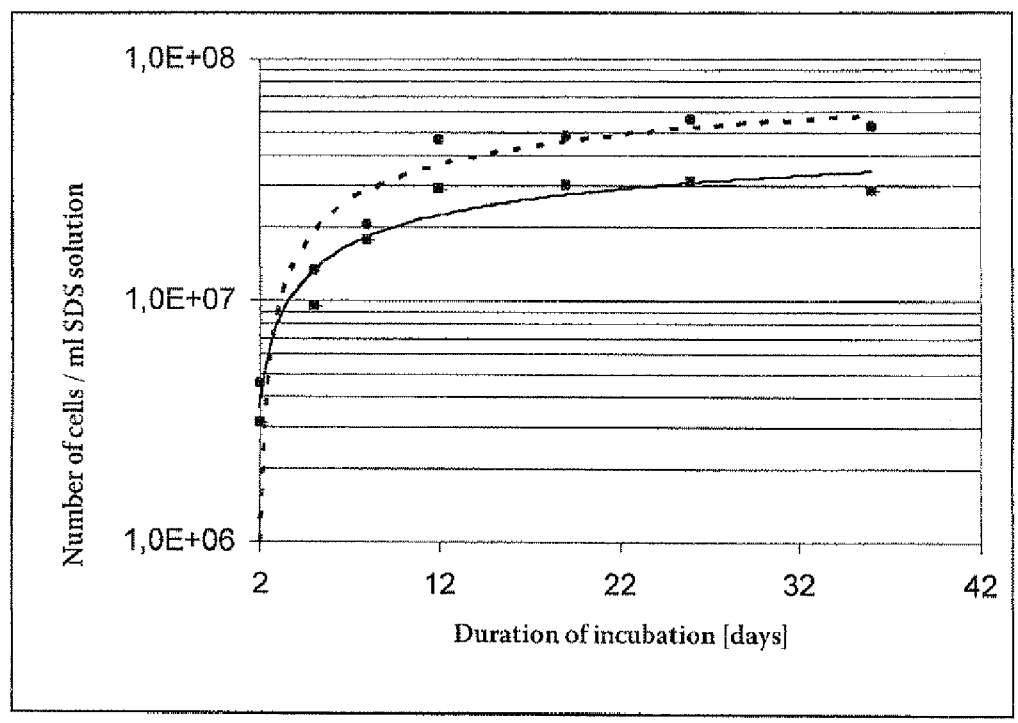

FIG. 2, as in FIGS. 2a and 2b, shows the growth behavior of the HEK 293 cells in SCS capsules at various points in time. Hereby the capsules were cultivated in DMEM medium with a 4.5% glucose (w/v) (Gibco, Glasgow) and 10% fetal calf serum (FCS) (Gibco, Glasgow) for a time period of 36 days. Aliquots were taken at various times.

FIG. 2a qualitatively shows, from left above to right below, the increase in the number of cells in the microcapsules, whereby samples were taken on days 1, 2, 3, 7, 14 and 21 after encapsulation. A watery SCS solution (2% w/v) used for encapsulation initially contained $2 \times 10^6$ cells/ml and in addition 1% NaCl (w/v). Other parameters for encapsulation were:

Concentration of the pDADMAC solution: 1.1% (w/v), Desired diameter of the capsule: 600 µm, Diameter of the nozzles: 200 µm, Volume current: 6.1 ml/min, Amplitude: 100%, Frequency: 900 Hz and Dispersion voltage: 1100 V.

FIG. 2b shows growth behavior of the encapsulated HEK293 cells in the capsules with a desired diameter of 600 to 1200 µm under application of the MTT-test (Roche, Mannheim) for living, immobilized cells. For this the capsules were cultivated in T75-cell culture flasks for a time period of 36 days. The parameters for the encapsulation in 600 µm capsules (- -) correspond to those described under FIG. 2a. For the encapsulation in 1200 µm capsules (- -) the following parameters were used: The 2% SCS solution used for encapsulation initially contained $1.5 \times 10^6$ cells/ml and in addition 1% NaCl (w/v). Other parameters for the encapsulation were:

Concentration of the pDADMAC solution: 2.5% (w/v), Diameter of the nozzles: 300 µm, Volume current: 12.9 ml/min, Amplitude: 100%, Frequency: 600 Hz and Dispersion voltage: 1200 V.

Both curves cannot be compared directly, but both show an ideal logarithmic growth behavior of the HEK 293 cells. This on the face of it shows that neither the complexated SCS, nor the non-complexated SCS within the capsule have a cytotoxic effect or a negative influence on the encapsulated cells.

Figure 3:
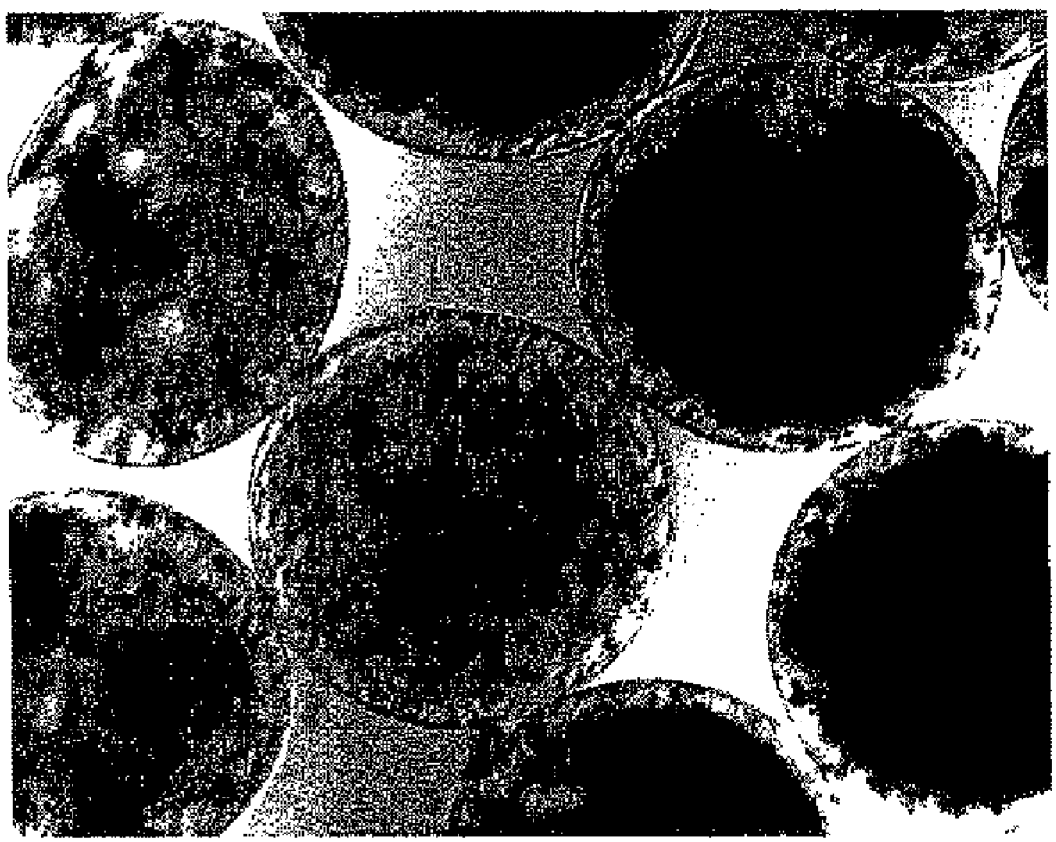

FIG. 3 shows a microscopic view of SCS capsules, which contain HEK 293-cells, after the deep-freezing and defrosting. The capsules were cultivated for 21 days in DMEM-medium with 4.5 g/l glucose (Gibco, Glasgow) and 10% fetal calf serum (Gibco, Glasgow) prior to the deep freezing. The deep freezing was carried out in DMEM medium with 10% DMSO (v/v). After an incubation period of 2 h the capsules were cooled down to −80° C. The defrosting process was carried out under slight agitation at 37° C. in a water bath. For a further cultivation the DMSO medium was repeatedly replaced by fresh DMEM medium in order to remove the excess DMSO. By means of the MTT-test it is possible to identify that the immobilized cells have survived the freezing and thawing procedure despite the high density of the cells within the capsule and that they can be cultivated further. After the defrosting the macroscopic structure of the membrane and the geometry of the capsule remained intact.

FIG. 4 shows the $^{13}C$ NMR spectrum of batch b2 of example 1b2. As a result of the regioselective substitution of the hydroxyl group by a sulfate group at the $C_6$ position, the signal is shifted from 60 to 67 ppm. No acetate groups or any substitution of sulfate groups at $C_2$ or $C_3$ positions could be detected. The DS value determined ($DS_6$=0.4) shows good agreement with the calculated DS value from the sulfur determination.

The following embodiments or examples are not to be taken as limitations of the invention. Further in the context of the description, the examples or embodiments such variations, elements and combinations have been openly credited, which either in combination or modification of themselves have the characteristics contained in the general description, in the examples, the claims or the diagrams although or even if these combinations of characteristics or changes are not explicitly shown or described in an embodiment, but lead to a changed subject or to new steps in the process, namely a new sequence of process steps.

EXAMPLES

Example 1

Production of Sodium Cellulose Sulfate (SCS)

Example 1a 10.7 g cellulose of 93.73% dry content (cotton linters with a Cuoxam-DP of 1230) is given to 333 ml dimethylformamide (DMF). The cellulose is swelled at room temperature for a time period of approximately 14 h.

The mixed esterification is started, after a successful swelling, by adding the reaction mixture, which is made of 8 mol/mol anhydroglucose unit (AGE) acetic acid anhydride (47 ml) as acetylating agent and 0.7 mol/mol AGU chlorosulfonic acid (2.9 ml) as sulfating agent as well as 100 ml DMF. The synthesis is carried out at a temperature of 50° C. The cellulose starts to dissolve and after about 3 h a clear transparent polymer solution is available.

After 5 h the neutralization/precipitation is carried out under constant stirring by slowly pouring the polymer solution (within approx 15 min) into a neutralization/precipitating medium, which is made up of 42.9 g sodium hydroxide (NaOH), 80 g $H_2O$ and 20 g sodium acetate filled up to 1.5 l with ethanol and has preferably at room temperature. After the polymer solution has been completely poured into the neutralization/precipitation medium it is stirred for another 1 h. Subsequently it is filtered, and washed thrice, each time with 600 ml washing solution consisting of 4% (w/w) sodium acetate in ethanol-water mixture (1:1, w/w).

Subsequently the deacetylation is carried out by adding 333 ml deacetylation reagent (13 g NaOH, 27 g $H_2O$ filled up to with 333 ml ethanol). The mixture is stirred for about 1 h and allowed to stand for about 12 h. The neutralization of the mixture is brought about by adjusting the pH-value to 8.0 with an acetic acid-ethanol mixture (1:1, w/w). Subsequently it is washed thrice with 1 l ethanol. It is dried at 40° C. in a vacuum.

The proportion and the quantity of the acetylating and sulfating agents used are dependent on the desired regio-selective substitution at the $C_2$, $C_3$ and $C_6$ positions. Suitable proportions of the mixture are known to those skilled in the art. The SCS obtained is clearly soluble in water and has a DS=0.33 and a viscosity of 25 mPas in a 1% aqueous solution.

The following methods were used for analytical characterization of the cellulose sulfate according to the invention:

A. Determination of Sulfur by Elemental Analysis:

After quantitative combustion of the SCS samples, the elements C, H, N and S were determined in % by means of elemental analysis (equipment from Carlo Erba), where the degree of substitution of sulfate ester groups is calculated from the sulfur content (taking into account the moisture content of the preparation) in accordance with $$DS_{sulfate} = 162 \times \% \, S/(3200 - 102 \times \% \, S)$$

B. Trace Metal Analysis Using Optical Emission Spectrometry:

The analysis was made after special pulping of the cellulose and cellulose derivatives by means of ICP-OFS (Inductively Coupled Plasma Optical Emission Spectrometry; Perkin-Elmer).

C. Total DS, Partial DS in C6 Position, Detection of Complete Removal of Acetyl Groups by Liquid $^{13}C$ NMR:

The partial degree of substitution in the individual positions of the AGU is calculated from the liquid $^{13}C$ NMR spectra of sodium cellulose sulfate solutions in $D_2O$ by integrating the signal areas and comparing the surface integrals of substituted and non-substituted SCS. The spectra were measured using a Bruker MSL 400 spectrometer at a frequency of 100.63 MHz, where tetramethylsilane was used as a reference for the chemical shift, D. Clear Solubility of Aqueous Cellulose Sulfate Solutions:

In addition to the optical evaluation of 1% aqueous solutions of the sodium cellulose sulfate, the turbidity value at an angle of 90° is measured in a type 2100AN turbidimeter (Hach-Lange GmbH, Düsseldorf, Germany) in NTU (Nephelometric Turbidity Units).

E. Solution Viscosity:

The kinematic viscosity of 1% aqueous solutions of the sodium cellulose sulfate is measured at 25° C. in a Viscoboy 2+SAE/KM2 automatic capillary viscosimeter (Lauda, Germany). The viscosities are given in mPas after conversion using the density.

Example 1.b1 and 1.b2

21.1 g of cotton linters (94.86% dry content, DP=1264) is slowly added to 550 ml of DMF (Dimethylformamide) under constant stirring at 80° C. for 8 h, cooled down to room temperature (RT) and agitated for further 12 h. After swelling a mixed esterification was started by adding the reagent mixture consisting of 8 mol/mol anhydroglucose units (AGU) of acetic acid anhydride (93 ml) and 0.9 mol/mol AGU of chlorosulfonic acid (7.4 ml) made up to a total volume of 200 ml with DMF. The reagent mixture was then added rapidly to the cellulose solution at 50° C. whilst stirring rapidly. As a result of the formation of cellulose acetate sulfate, a yellowish transparent polymer solution was obtained after approximately 1.5 h. After 4.5 h the batch was divided in two portions. Half of the polymer solution was removed and added to neutralization and precipitation medium, consisting of 42.9 g NaOH, 80 g $H_2O$ and 20 g of sodium acetate made up to a volume of 1.5 l with ethanol (b1). The other half (b2) was agitated for a further 3.5 h at 50° C. and then added to neutralization and precipitation medium. After precipitation had taken place, both batches were filtered separately and washed three times with 600 ml washing solution (4% sodium acetate (w/w) in ethanol-water mixture (1:1, w/w)). Deacetylation was started by adding 333 ml of a deacetylation reagent (13 g NaOH, 27 g $H_2O$ made up to a volume of 333 ml with ethanol). Both batches were agitated for 1 h and left to stand for about 12 h at room temperature. The pH was adjusted using an acetic acid-ethanol mixture (1:1, w/w). Both cellulose sulfate preparations were then washed three times with 1 l of ethanol in each case and dried at 40° C. in a vacuum. The properties of the SCS obtained are given in Table aa. FIG. 4 shows the $^{13}C$ NMR spectrum of batch b2. As a result of the regio-selective substitution of the hydroxyl group by a sulfate group at the C6 position, the signal is shifted from 60 to 67 ppm. No acetate groups or any substitution of sulfate groups at $C_2$ or $C_3$ positions could be detected. The DS value determined ($DS_6$=0.4) shows good agreement with the calculated DS value from the sulfur determination.

TABLE aa

|  | Batch b1 | Batch b2 |
| --- | --- | --- |
| Reaction time [h] | 4.5 | 8 |
| Mass [g] | 12.1 | 10.7 |
| Dry content [%] | 84.11 | 85.31 |
| Sulfur content [%] | 7.99 | 7.24 |
| Degree of substitution (DS) | 0.54 | 0.48 |
| Regio-selectivity | C6 | C6 |
| Viscosity [mm/s$^2$] | 66 | 14 |

Example 1.c1 and 1.c2

As described in Example 1b, two different SCS formulations were prepared using different starting chemicals. In batch c1 no attention was paid to the metal content of the starting chemicals. The weighing or addition of chemicals was carried out using metal spatulas. A metal agitator was used for the precipitation process. In batch c2 only chemicals having extremely low metal contents were used. In addition, any contact with metal-containing equipment such as agitators, spatulas etc. was avoided during synthesis. The analysis of the heavy metal contents of both formulations is given in Table bb.

TABLE bb

|  | Heavy metals | | | | | |
| --- | --- | --- | --- | --- | --- | --- |
|  | Cu | Ni | Ti | Mn | Zn | Fe |
| Formulation c1 (in ppm) | 3 | 2 | 1 | 0 | 37 | 12 |
| Formulation c2 (in ppm) | 1 | 0 | 1 | 0 | 0 | 2 |

Example 1.d1

The same procedure as in Example 1b is followed except that instead of cotton linters, a ground cellulose powder Arbocell M80 from Rettenmayer (Germany) was used. 21.2 g Cuoxam (DP=750, Dry content=94.16%) were converted with 11 mol/mol anhydroglucose units (AGU) of acetic acid anhydride and 1 mol/mol AGU of chlorosulfonic acid in 200 ml DMF. After deacetylation, the product obtained was purified by dialysis and subsequently freeze dried. The clear soluble sodium cellulose sulfate (SCS) obtained in water has a DS=0.49 and a 1% aqueous solution has a viscosity of 15 mPas.

Example 1.d2

Cotton linters were used like in Example 1a but instead 11 mol/mol anhydroglucose units (AGU) of acetic acid anhydride and 1.1 mol/mol AGU of chlorosulfonic acid in 200 ml DMF was used. The clear soluble sodium cellulose sulfate (SCS) obtained in water has a DS=0.57 and a 1% aqueous solution has a viscosity of 120 mPas.

Example 1.e1 and 1.e2

Sodium cellulose sulfate (SCS) was produced as described in Example 1a. Additionally the synthesis steps after the deacetylation were carried out as described in Example a1 but for example e2 this was carried out in a laminar box for comparison of the degree of contamination. The results are presented in Table dd.

The sterility test was carried out in accordance with the recommendation of the "European Pharmacopoeia 4" in the liquid media "thioglycollate medium" for anaerobic microorganisms and "trypticase soy broth" for aerobic micro-organisms. In addition, the low-nutrient liquid medium "¼ strength peptone yeast extract broth" was also used. After preparing the nutrient medium, 10 ml at a time was poured into screw-top vials. These were then autoclaved at 121° C. Each vial was inoculated with 1 ml of sample and then temperature-controlled for 14 days at 28° C. Each test was carried out using a double formulation. As a sterile control two non-inoculated vials of each medium were used under the same conditions.

Those vials in which turbidity or sediment was observed were regarded as contaminated. Sample e2, which was prepared under sterile conditions showed no turbidity or sediment and was considered to be bacteria-free.

TABLE dd

| Medium | Thioglycollate broth (anaerobic) | | Trypticasesoy broth (aerobic) | | ¼ strength peptone yeast extract broth (aerobic) | |
|---|---|---|---|---|---|---|
| Sample | I | II | I | II | I | II |
| e1 | ++ | − | ++ | ++ | + | + |
| e2 | − | − | − | − | − | − |

Legend:
− No growth after incubation for 14 days
+ Growth after incubation for 14 days
++ Strong growth after 14 days

Example 1.f 10.7 g of cotton linters (TG=93.9%, DP=1351) was added to 230 ml of DMF and as described in example 1a and was allowed to swell while stirring continuously for 8 h. The starting temperature was adjusted to 80° C. After cooling to room temperature the mixture was kept without stirring for a further 12 h. After swelling had taken place, mixed esterification was started by adding the reagent mixture. The reagent mixture was produced separately by cooling and agitating by successively adding 11 mol/mol anhydroglucose units (AGU) of acetic acid anhydride (64 ml) and 1 mol/mol AGU of sulfuryl chloride (5 ml) to 100 ml of DMF. The reagent mixture was then added rapidly to the cellulose whilst stirring continuously. Subsequently the reaction temperature is brought to 50° C. After 6 h the neutralization and precipitation takes place by slowly (in about 15 min) adding—still continuously stirring—the polymeric solution to the neutralization and precipitation medium, consisting of 42.9 g NaOH, 80 g $H_2O$ and 20 g of sodium acetate made up to a volume of 1.5 l with ethanol and which has preferably room temperature. After the polymeric solution had been added to the neutralization and precipitation medium the whole mixture was stirred for one further hour. Subsequently the formulation was filtered, and washed three times with 600 ml in each case using a washing solution (4% w/w) of sodium nitrate in an ethanol-water mixture (1:1, w/w). Deacetylation took place by adding in each case 333 ml of deacetylation reagent (13 g NaOH, 27 g $H_2O$ made up to a volume of 333 ml with ethanol). The formulation was agitated for 1 h and left to stand for about 12 h at room temperature. The pH was then adjusted to 8.0 using an acetic acid-ethanol mixture (1:1, w/w). Then the formulation was washed three times with 1 l of ethanol and dried at 40° C. in vacuum. The resulting SCS has a sulfur content of 6.49%, which results in a degree of substitution DS=0.51. The DS value determined by using NMR ($DS_{total}=DS_{C6}$) was 0.55. A 1% aqueous solution has a viscosity of 40 mPas ($mm^2/s$).

Example 1g

The same procedure as in example 1f is followed except that 250 ml N-methyl-2-pyrrolidone (NMP) was used as solvent. The mixed esterification was started, after swelling by adding the reaction mixture, which consists of 11 mol/mol anhydroglucose units (AGU) acetic acid anhydride (64 ml) as acetylating agent and 0.5 mol/mol AGU amidosulfuric acid (2.9 ml) as sulfating agent and 100 ml N-methyl-2-pyrrolidone (NMP). The synthesis was carried out at a temperature of 70° C. The precipitation, deacetylation, washings and drying of the product is performed as described in example 1f. The resulting, in water clearly soluble SCS has a sulphur content of 5.12% (DS=0.31). The DS value determined by using NMR ($DS_{total}=DS_{C6}$) resulted in 0.33. A 1% aqueous solution has a viscosity of 12 mPas.

Example 1h

The same procedure as in example 1f is followed except that 350 ml N,N-dimethyl acetamide (DMAc) are used as solvent. The mixed esterification is started, after swelling by adding the reaction mixture, which is made of 11 mol/mol anhydroglucose units (AGU) acetic acid anhydride (64 ml) as acetylating agent and 0.9 mol/mol AGU sulfuric acid (3 ml, 98% $H_2SO_4$) as sulfating agent as well as 150 ml DMAc. The synthesis is carried out at a temperature of 70° C. The precipitation, deacetylation, washings and drying of the product is performed as described in example 1f. The resulting, in water clearly soluble SCS has a sulfur content of 6.93% (DS=0.45). A 1% aqueous solution has a viscosity of 5 mPas.

Example 1i

The same procedure as in example 1f is followed except that 350 ml N,N-dimethyl acetamide DMAc are used as solvent. The mixed esterification is started, after swelling by adding the reaction mixture, which is made of 6 mol/mol anhydroglucose units (AGU) acetyl chloride (29 ml) as acetylating agent and 1.5 mol/mol AGU sulfuric acid (4.9 ml) as sulfating agent as well as 150 ml DMAc. The synthesis is carried out at a temperature of 70° C. The precipitation, deacetylation, washings and drying of the product is performed as described in example 1f. The resulting, in water clearly soluble SCS has a sulfur content of 10.73% (DS=0.82). A 1% aqueous solution has a viscosity of 13 mPas and a value of turbidity of 2.5 NTU.

Example 1j

The same procedure as in example 1f is followed except that 350 ml NMP are used as solvent. The mixed esterification is started, after swelling by adding the reaction mixture, which is made of 6 mol/mol AGU acetyl chloride (29 ml) as acetylating agent and 1.5 mol/mol AGU $SO_3$/DMF complexes (14 g, commercially available as 1:1 complex) as sulfating agent as well as 150 ml NMP. The synthesis is carried out at a temperature of 60° C. The precipitation, deacetylation, washings and drying of the product is performed as described in example 1f. The resulting, in water clearly soluble SCS has a sulfur content of 9.83% (DS=0.72). A 1% aqueous solution has a viscosity of 12 mPas and a value of turbidity of 6.6 NTU.

Example 2

Manufacture of SCS Microcapsules from SCS as Per the Invention

In accordance with the known methods (AirJet-method; JetCutter-method; Vibration method) for preparing the microcapsules (Orive et al., 2004, Trends Biotechnol, 10 22 (2): 87-92), the cellulose-sulfate solution was added dropwise for complexation in a polycation solution (e.g. pDADMAC) with the help of an encapsulation device (Inotech, Model IE-50).

The immersion of a cellulose-sulfate droplet in a stirred aqueous solution of a polycation (pDADMAC) leads to the formation of a semi-permeable membrane at the phase interface through a spontaneously running complexation reaction, which encloses a non-complexed, liquid core. With progressive reaction time, the membrane strength increases through diffusion of the polycation in the capsule membrane for so long, till the density of the forming three-dimensional network creates a diffusion barrier for the polyelectrolyte.

For making the capsules, a homogeneous aqueous solution of SCS with a cellulose-sulfate concentration of 1.5-3.5% (w/v) is generated. The SCS used for this had a degree of substitution (DS) between 0.3 and 0.99. This SCS solution was added drop-wise in a 0.8-2% pDADMAC-solution (w/v) with a laminar flow speed of 1-15 ml/min through a 100-300 µm nozzle. Owing to the low structural viscosity with a high surface tension at the same time of the SCS-solution as per the invention, a high working speed is possible. The drop formation and the drop size is determined for one by the volume flow, the physical fluid characteristics, the selection of the nozzle diameter and, in case of the vibration method also by the excitation frequency and the frequency amplitude, with which the decomposition of the liquid jet in drops is controlled. This frequency was set to 600-1100 Hz, in order to generate spherical microcapsules with a diameter of about 650-700 µm. Increasing the frequency results in smaller capsule sizes, and the size becomes bigger if the frequency is lowered. Preferably, a frequency of 650 Hz is selected for generating capsules having an average size of 700 µm diameter with a 250 µm nozzle. A frequency of 1100 Hz is to be selected for generating capsules with an average size of 500 µm, and a frequency of 500 Hz for generating capsules with an average size of 800 µm. A fine-tuning is possible by modulating the other parameters.

Furthermore, the size of the capsules is also influenced by the reaction of the cellulose sulfate with the pDADMAC. Increased reaction time, high concentrations and a low molecular weight of the pDADMAC reduce the capsule size. It could be shown that the symplex-microcapsules, which are prepared with the SCS as per the invention, show a reproducible and a quasi-ideal, spherical geometry and at the same time a low size scattering (FIG. 1)

Example 3

Manufacture of SCS-Capsules with Biological Objects

The process of manufacturing SCS-microcapsules includes as the important steps (a) the preparation of the SCS-solution, (b) the preparation of the SCS-cell suspension, (c) the conversion of the capsules in drops, (d) the complex formation in the complexation bath and (e) the termination of the complex forming reaction.

The SCS as per the invention is first dissolved in physiological buffered salt solution (0.8-1.0% (w/v)) in a concentration of 1.5-3.5% (w/v) under stirring at room temperature and the pH-value is adjusted to 7.2 with 0.1N NaOH or 0.1N HCl. The prepared SCS-solution is autoclaved at 121° C. before mixing with the cells.

Preparation of SCS-Cell Suspensions:

For encapsulating the SCS-capsules, HEK293-cells (ATCC CRL-2828), Jurkat-cells (ATCC TIB-152) or the HIT-cells (ATCC CRL-1777) are used. In principle, however, a number of adherent as well as suspension cells can be used. The cell cultures are multiplied exponentially in suitable, conventional cell-culture methods e.g. in T75-Flasks or roller bottles and are reaped after the formation of a mono-layer at 90% confluence. The cell lines used are incubated in DMEM-medium with 4.5 g/l glucose (Gibco, Glasgow, UK) with 10% fetal calf serum (Gibco, Glasgow, UK). The released cells are transferred in a 50 ml Falcon-tube, centrifuged for 5 minutes at 200 g and the supernatant fluid is thrown away. The cell pellet is then carefully washed with the PBS-buffer and finally in integrated in SCS-solution, suspended homogeneously in SCS-solution, transferred into a sterile syringe and subsequently connected under sterile conditions, to the encapsulation unit equipped with all the hose connections and vessels, which are autoclaved. The encapsulation process starts directly thereafter.

Conversion to Drops and Capsule Production:

For encapsulation, the speed is first increased to such an extent that a uniform liquid current flows out of the capillary; thereafter the volume flow can be reduced to the speed optimum for a conversion in drops. The waste SCS-cell suspension, converted to drops till this time, is intercepted by a swiveling catchments tank before falling in a hardening bath, which is swiveled to the side after the formation of a uniform liquid jet (stable phase), so that the capsule formation can take place. The generated microcapsules can be pumped out continuously from the reaction area and should be washed or diluted with physiological buffered salt solution, PBS (phosphate buffered saline) or the culture medium, in order to remove the non-complexated pDADMAC. All steps can be done under sterile conditions.

Thereafter, on a sterile workplace, the supernatant fluid is taken out of the collective vessel by means of a pipette, after the capsules have sedimented and is replaced by the culture medium. Directly thereafter, the encapsulated cells are cultivated in T-flasks or in roller bottles at 37° C., 5% $CO_2$, saturated humidity and 2 rpm. After 4 to 8 h, the medium is changed once again, in order to remove the remaining pDADMAC. While preparing the capsules, attention must be paid to the sterility of all components and solutions.

Determination of Vitality Through Trypane-Blue Coloration:

The determination of vitality through trypane-blue coloration serves for determining the total cell count (dead and living cells). Trypane-blue (0.8 mM in PBS (Sigma-Aldrich, Deisenhofen, Germany) is a negatively charged coloring agent, which can selectively diffuse in the cells with a non-intact cell membrane and can give a blue coloring to its cytoplasm. As a result, dead cells appear blue-violet under the light microscope, whereas the living cells have a white to yellowish color. The count of the living and the dead cells can then be determined with the help of a Neubauer-counter chamber microscopically.

Vitality Determination with the Help of the MTT-Test

The determination of vitality with the help of the MTT-Test (MTT-Proliferation Kit, Roche, Mannheim, Germany) includes only the living cell count contrary to the trypane-blue coloring described above.

This measurement method is a calorimetric test, in which the yellow tetrazolium salt 3-[4,5-dimethylthiazole-2-yl]-2, 5-diphenyl-tetrazolium-bromide (MTT) is absorbed passively in the living cells and is reduced to purple formazan crystals, insoluble in water, by the action of dehydrogenases. The quantity of the formazan formed is proportional to the living cell count at a constant and sufficiently long incubation period. The determination is done photometrically at $\lambda=570$ nm after an incubation period of 4 h at 37° C.

MTT-Vitality Test for Encapsulated Cells

The MTT test was developed originally to determine the living cell count of the cell suspensions. A qualitative MTT-test can also be done at the intact capsules. But, for the quantitative determination, the cells must be dissolved out of the capsules by incubating the capsules for 1 h in 20% SDS-solution (Sigma-Aldrich, Germany) in ultrasonic bath. The capsule and cell fragments still available are centrifuged. The MTT-test was performed according to the instructions of the supplier MTT-Proliferation Kit, Roche, Mannheim, Germany). The MTT-concentration is measured spectrophotometrically.

Example 4

Determination of the Reproducibility of the Capsule Quality With the Use of Different SCS-Manufacturing Batches For producing 600 µm capsules, a 2% SCS (w/v) solution is prepared with 1% NaCl (w/v) and a 1.0% pDADMAC (w/v) solution with 1% NaCl (w/v). The pDADMAC solution is tempered to 30° C., 20 ml of SCS are added drop-wise in 300 ml of a stirred, 1.0% pDADMAC-solution. The reaction time is 3 min.

The nozzle diameter is 200 µm. The volume flow is 6.1 ml/min. The amplitude of the nozzle vibration is set to 100%, the frequency is set to 900 Hz. The dispersion voltage is 1100 V.

For producing 600 µm capsules with immobilized cells, the method as described under example 3 is adapted. In addition, the cells growing confluent to 90% are trypsinated in a T75-Flask, absorbed in NM-medium (DMEM-medium with 4.5 g/l glucose+10% FCS (Gibco, Glasgow, UK)) and pelletised at 200 g for 5 min. The pellet is suspended again in PBS and the cell concentration is determined. An aliquot of the cell suspension is pelletised, in order to achieve a cell concentration of $2 \times 10^6$ cells/ml SCS. The washed pellet is suspended again in the SCS-solution and is filled in an injection. The conversion of the cell suspension to drops takes place directly thereafter.

Determination of Capsule Size:

The capsule sizes are determined microscopically in a Neubauer-counting chamber (light microscope M 200 and software "Zeiss Imaging Vers. 4" (Carl Zeiss Jena, Jena, Germany) under 4× magnification.

Stability Measurement of Microcapsules:

For determining the mechanical properties of the SCS-microcapsules, a force-displacement measuring device (LU-MiTexture, Lerche GmbH, Berlin, Germany) was used.

A stamp applies load to the test object with a programmable speed, while an electronic scale measures the resulting force. From the force-displacement curve, the parameters of burst pressure and the maximum tension appearing in the symplex-membrane can be determined. Stability measurements are used for capsules without immobilized cells as well as also for studying the long-term stability of capsules with immobilized cells.

TABLE 2

|  | Manufacturing batch | | | |
| --- | --- | --- | --- | --- |
|  | 1 | 2 | 3 | 4 |
| Average maximum stress [N/m] | 1.36 | 1.43 | 1.35 | 1.38 |
| Standard deviation [N/m] | 0.27 | 0.29 | 0.22 | 0.20 |
| Number of samples | 20 | 20 | 20 | 20 |

The measurement of capsules, with the same encapsulation parameters, but prepared with 4 different production batches shows that the capsule stabilities achieved are absolutely comparable. The average stabilities vary by about 6%. The scattering between the individual batches is lower than the standard deviation of the respective measurement ranges. This result illustrates that the complex-forming reaction, through which the formation of the symplex-membrane runs, can be controlled very well owing to the reproducible SCS-synthesis and the selected process management. The constantly high capsule stability enables an estimation of the usability of the capsules produced for special purposes with high mechanical loads and thus minimizes the risk of a mechanical damage to the capsules. The capsules are adequately stable for cultivation in resting and stirred culture vessels, as well as for intravenous injections and for implanting in the human and animal tissue.

Example 5

Effect of the Encapsulated Cells on the Capsule Stability

The capsule preparation was done as described under example 3. The stability was measured according to the process mentioned in example 4. The capsules were initially loaded with 300 cells/capsules. The measurement was done 14 days later.

TABLE 3

| Sample | Without cells | With cells |
|---|---|---|
| Average maximum stress [N/m] | 1.43 | 1.45 |
| Standard deviation [N/m] | 0.29 | 0.26 |
| Number of samples | 20 | 20 |

If the suspended cells lie at the surface of the droplet, then it can happen that they are fixed permanently in the membrane during the complexation reaction between SCS and pDADMAC. The measured capsule stabilities illustrate that the cells suspended in SCS do not negatively influence the stability of the capsule membrane. This is a basic pre-requisite for the immobilization of the non-soluble solids, such as tissues, human and animal cells, micro-organisms, micro-particles, nano-particles, immobilized enzymes, catalysts and crystalline substances insoluble in water.

Example 6

Long-Term Stability of SCS Capsules with Immobilized Cells

The capsules are prepared and cultivated according to the method described in example 3. The stability measurements are done as described under example 4. Initially, 300 cells/capsule are encapsulated and are cultivated for 60 days in DMEM-medium with 4.5 g/l glucose+10% fetal calf serum (Gibco, Glasgow, UK) at 37° C. and 5% $CO_2$ in roller bottles at 2 rpm.

TABLE 4

| Sample | shortly after preparation | After 60 days in culture |
|---|---|---|
| Average maximum stress [N/m] | 1.35 | 1.11 |
| Standard deviation [N/m] | 0.22 | 0.20 |
| Number of samples | 20 | 20 |

The measurements of the maximum stress within the capsule membrane, which appears just before the destruction of the capsules, shows that the capsule stability falls by 18% over a cultivation duration of 60 days, but is still sufficiently high to preserve the integrity of the capsules. The symplex membrane formed is resistant to osmotic, chemical and physical stress, which occurs during the cultivation of the immobilized cells in the cell-culture medium. This enables a use in high salt concentrations, changing pH-values and under permanent mechanical stress.

Example 7

Manufacture and Reproducibility of SCS-Microcapsules with a Specified Diameter

For preparing capsules with a reference diameter of 250 µm, a 1.5% SCS (w/v) solution is prepared with 1% NaCl (w/v) and a 0.85% pDADMAC (w/v) solution is prepared with 1% NaCl (w/v). The pDADMAC solution is tempered to 30° C. 10 ml of SCS are added drop-wise in 300 ml of a stirred 0.85% pDADMAC solution. The concentration ratio pDADMAC to SCS is 17 (g/g). The reaction time is 2 min.

The injection drive is equipped with 10 ml plastic injections. The nozzle diameter is 100 µm. The volume flow is 1.5 ml/min. The amplitude of the nozzle vibration is 100%, the frequency is set to 2000 Hz. The dispersion voltage is 1300 V. The results are shown in FIG. 1A.

For preparing capsules with a reference diameter of 520 µm, a 1.8% SCS (w/v) solution with 1% NaCl (w/v) and a 1.0% pDADMAC (w/v) solution is prepared with 1% NaCl (w/v). The pDADMAC solution is tempered to 30° C. 20 ml SCS is added drop-wise in 300 ml of a stirred, 1.0% pDADMAC-solution. The concentration ratio of pDADMAC to SCS is 11.1 (g/g). The reaction time is 3 min.

The injection drive is equipped with plastic injections. The nozzle diameter is 200 µm. The volume flow is 6.1 ml/min. The amplitude of the nozzle vibration is 100%, the frequency is set to 1100 Hz. The dispersion voltage is 1100 V. The results are shown in FIG. 1B.

For preparing capsules with a reference diameter of 700 µm, a 2.8% SCS (w/v) solution with 1% NaCl (w/v) and a 1.5% pDADMAC (w/v) solution is prepared with 1% NaCl (w/v). The pDADMAC solution is tempered to 30° C. 15 ml SCS is added drop-wise in 8.5 ml of a stirred, 1.5% pDADMAC solution. The concentration ratio of pDADMAC to SCS is 10.7 (g/g). The reaction time is 3 min.

The injection drive is equipped with plastic injections. The nozzle diameter is 250 µm. The volume flow is 8.5 ml/min. The amplitude of the nozzle vibration is 100%, the frequency is set to 700 Hz. The dispersion voltage is 1100 V. The results are shown in FIG. 1C.

For preparing capsules with a reference diameter of 1200 µm, a 2% SCS (w/v) solution with 1% NaCl (w/v) and a 2.5% pDADMAC (w/v) solution is prepared with 1% NaCl (w/v). The pDADMAC solution is tempered to 30° C. 30 ml SCS is added drop-wise in 300 ml of a stirred, 2.5% pDADMAC solution. The concentration ratio of pDADMAC to SCS is 10.7 (g/g). The reaction time is 5 min.

The injection drive is equipped with plastic injections. The nozzle diameter is 300 µm. The volume flow is 12.9 ml/min. The amplitude of the nozzle vibration is 100%, the frequency is set to 600 Hz. The dispersion voltage is 1200 V. The results are shown in FIG. 1D.

The capsule sizes are determined microscopically in a Neubauer-counting chamber (light microscope M 200 and software "Zeiss Imaging Vers. 4" (Carl Zeiss Jena, Jena, Germany) under 4× magnification.

Determination of the Reproducibility of the Capsule Size With the Use of Different SCS-Manufacturing Batches To compare the reproducibility of different manufacturing batches of SCS capsules with a reference diameter of 710 µm are prepared, using a 1.7% SCS (w/v) solution with 1% NaCl (w/v) and a 1.5% pDADMAC (w/v) solution with 1% NaCl (w/v). The pDADMAC solution is tempered to 30° C. 15 ml SCS is added drop-wise with 8.1 ml/min into 300 ml of a stirred, 1.5% pDADMAC solution. The concentration ratio of pDADMAC to SCS is 10.7 (g/g). The reaction time is 3 min.

The injection drive is equipped with plastic syringes. The nozzle diameter is 250 µm. The volume flow is 8.1 ml/min. The amplitude of the nozzle vibration is 100%, the frequency is set to 750 Hz. The dispersion voltage is 1350 V. The results are shown in Table 5.

The capsule sizes are determined microscopically in a Neubauer-counting chamber (light microscope M 200 and software "Zeiss Imaging Vers. 4" (Carl Zeiss Jena, Jena, Germany) under 4× magnification.

TABLE 5

| | Manufacturing batch | | | | |
|---|---|---|---|---|---|
| | 1 | 2 | 3 | 4 | 5 |
| Mean diameter [μm] | 667 | 725 | 714 | 720 | 717 |
| Standard deviation [μm] | 16 | 29 | 26 | 25 | 18 |
| Standard deviation [%] | 2.3 | 4.0 | 3.6 | 3.5 | 2.5 |
| Mean diameter of all batches [μm] | 709 | | | | |
| Mean standard deviation of all batches | 24 μm (3.3%) | | | | |

Further manufacturing specifications correspond to the method described in example 2.

The examples shown in FIG. 1 illustrate that the mono-dispersed SCS-microcapsules can be manufactured with different diameters, which opens up a broad spectrum of the usage possibilities of the capsules. The standard deviation of the capsule diameter is low at 4% in the mean. The batch-to-batch variation is low at 3.3% for capsules having a diameter of 710 μm therefore a high reproducibility when using SCS produced with the process of the invention on-hand is achievable. This is due to the fact that the liquid jet streaming out of the nozzle has a constant flow rate, which is possible only with very homogeneous polymer solutions. This is especially of high relevance for the preparation of the capsules with a lower diameter, because small changes in flow rate lead to high variations in capsule size. Even at a low average diameter of 265 μm, a standard deviation of 4% is reached with the SCS of the invention on-hand (FIG. 1a), although minimum volume changes caused by inhomogeneous SCS-solutions can have a dramatic negative effect on size distribution. At 520 μm capsules, a standard deviation of 2% can be realized (FIG. 1b). The mono-dispersal of the capsules produced enables a very accurate dosage of the immobilized material, because the surface of the capsules can be calculated exactly. The immobilized cells grow in mono-dispersed particles uniformly. In the case of agitated cultivation vessels, the mono-dispersed capsules guarantee a uniform dispersion and hence an optimum growth condition for all cultivated cells. An application of microcapsules using a cannula is possible only for capsules with low size scattering, because these minimize the risk of blocking. Higher nozzle diameters permit the immobilization of small isolated tissues with a minimum blocking risk, Mono-dispersed capsules can be prepared with these, too (FIG. 1C). The minimum size of the capsules that can be manufactured is only limited by the method chosen for drop generation and not by the SCS-solution used.

Example 8

Investigations on the Influence of SCS Capsules Regarding the Growth Behavior of Cells The growth behavior of HEK 293 cells was conducted in a time course experiment.

For the production of the SCS capsules, dividing cells of a T75-Flask at 90% confluency were trypsinized, collected in DMEM-medium and centrifuged with 200 g for 5 min. The mass was resuspended in PBS and the cell concentration was determined. An aliquot of the cell suspension was pelletised again to adjust a cell concentration of $2 \times 10^6$ cells/ml SCS. The washed pellet was resuspended in the SCS solution and filled into a syringe. The conversion of the cell suspension to drops took place directly thereafter.

For the production of 600 μm capsules 2% SCS (w/v) with 1% NaCl (w/v) and 1.1% pDADMAC (w/v) solution with 1% NaCl (w/v) was taken. The pDADMAC solution was kept at a moderate temperature of 30° C. 20 ml SCS solution were dripped in 300 ml of a stirred 1.1% pDADMAC solution. The reaction time was 3 min.

The nozzle diameter was 200 μm. The flow rate was adjusted to 6.1 ml/min. The amplitude of the nozzle oscillation amounted to 100%, the frequency was adjusted to 900 Hz. The dispersion voltage was 1100 V.

For the production of 1200 μm capsules 2% SCS (w/v), a solution of 1% NaCl (w/v) and a 2.5% pDADMAC (w/v) solution with 1% NaCl (w/v) was taken. The pDADMAC solution was heated to 30° C.

30 ml SCS solution was dripped in 300 ml of an agitated 2.5% pDADMAC solution. The reaction duration was 5 min. The nozzle diameter was 300 μm. The flow rate was 12.9 ml/min. Be amplitude of the nozzle oscillation was 100%, the frequency was adjusted to 600 Hz. The dispersion voltage was 1200 V.

FIG. 2a shows on the top left to the bottom right the quality of the increase of the cell count in the micro capsules, whereby test samples were taken on the days 1, 2, 3, 7, 14 and 21 after the encapsulation.

The FIG. 2a in the microscopic photographs clearly shows good cell growth of immobilized HEK 293 cells in SCS capsules. The cells were immobilized as single, non-agglomerated cells, attached in the beginning to the inner surface of the capsule membrane and finally fill the capsule. The cells then lie in dense, tissue-like cell agglomerations within the capsule lumen.

In FIG. 2b a growth curve of immobilized HEK 293 cells in capsules with 600 μm, and/or 1200 μm is shown. The graphs clarify the increase in encased HEK 293 cells during a period of 36 days. The capsules were cultured for this in T175-Flasks with 30 ml NM Medium. The living cell count per ml SCS solution was determined with the MTT test (MTT-Proliferation Kit, Roche, Mannheim, Germany) according to the instructions of the manufacturer.

The FIG. 2b further shows a logarithmic growth phase, which over an expanded transitional phase with decreased growth rate based on the encapsulation first, which is transformed into a final, stationary phase. Even using static cultivation very high cell densities of $5.61 \times 10^7$ cells per ml SCS were obtained with capsules having a diameter of 600 μm and $3.1 \times 10^7$ cells per ml SCS with capsules having a diameter of 1200 μm. The higher cell density in smaller capsules is proportional to the increased specific exchange surface, which limits the vague material transfer of gases and nutrients (Table 6).

TABLE 6

| $r_{sphere}$ [mm] | $A_{sphere}/V_{sphere}$ [mm$^2$/mm$^3$] | Cell density [cells/ml SCS] |
|---|---|---|
| 0.3 | 10.0 | 5.60E+07 |
| 0.6 | 5.0 | 3.10E+07 |

The measured duplication times ($t_D$) in the early logarithmic growth phase are as $t_{D\ 600\ \mu m}=73$ h and $t_{D\ 1200\ \mu m}=86$ h comparably high, since at this time diffusion is not yet a limiting factor for cell growth.

Example 9

Stability of SCS Capsules After Freezing and Thawing

For the tests dividing cells of a T75-Flask at 90% confluency were suspended in DMEM medium and centrifuged with 200 g for 5 min. The pellet was resuspended in PBS and the cell concentration was determined. An aliquot of the cell suspension was pelletised to adjust a cell concentration of $2\times10^6$ cells/ml SCS. The washed pellet was resuspended in the SCS solution and filled into a syringe. The encapsulation process was started directly there after.

For the production of 600 μm capsules, 2% SCS (w/v) with 1% NaCl (w/v) and 1.1% pDADMAC (w/v) solution with 1% NaCl (w/v) was taken. The pDADMAC solution was kept at a temperature of 30° C. 20 ml SCS was dripped in 300 ml of an agitated 1.1% pDADMAC solution. The reaction duration was 3 min.

The nozzle diameter was 200 μm. The flow rate was adjusted to 6.1 ml/min. The amplitude of the nozzle oscillation was 100%, the frequency was adjusted to 900 Hz. The dispersion voltage was 1100 V.

The capsules were cultured for 21 days before freezing in T175-flasks with 30 ml DMEM medium with 4.5 g/l glucose+10% FCS.

The freezing took place in DMEM medium with 4.5 g/l glucose+10% FCS to which additional 10% DMSO (v/v) was added. After an incubation time of 2 h the capsules were cooled down to −80° C. with a constant cooling rate. The capsules were stored at −80° C.' for further use The microscopic image (FIG. 3) shows capsules with immobilized cells, which had been defrosted and later cultivated in DMEM medium for 24 h, after live staining with the MTT-test (MTT-Proliferation Kit, Roche, Mannheim, Germany) according to the instructions of the manufacturer.

After defrosting, the macroscopic membrane structure of the capsules remains completely intact. The capsules kept the immobilized cells also after this procedure stable. As can also be seen by using the MTT test the immobilized cells survive the freezing and thawing procedure and can easily again be cultivated, despite very high cell density at the inside of the capsule. The capsule membrane appeared to be overall opaque. This makes it possible for one to provide capsules with high concentration of human cells by using industrial production methods. Also the storage as aliquots and a cryo conservation can be provided at reasonable expenses.

The invention claimed is:

1. Method for the production of regio-selective substituted cellulose sulfate (CS) characterized by a combination of the following steps:
   a) swelling of native cellulose in a polar aprotic solvent;
   b) addition of a sulfating reagent and an acetylating reagent, for the simultaneous esterification and distribution of acetate groups and sulfate groups along and between the polymer chains;
   c) directly followed by a complete neutralization with a base, whereby the sulfate without cleaving the acetyl group is transferred into a sodium salt of the cellulose acetate sulfate (SCS), whereby the directly following neutralization also avoids cleavage of acetate groups and consequently the degradation of the cellulose chains; and
   d) subsequent precipitation, deacetylation, washing and drying of the SCS, whereby the SCS is characterized by a solution viscosity, which is greater than 10 mPas at a concentration of 1% in water.

2. Method according to claim 1 characterized in that the neutralization step is accomplished at the same time with the precipitation.

3. The method as recited in claim 1, wherein the step of complete neutralization with a base adds a stoichiometric amount of base, relative to the sulfating reagent, to perform the complete neutralization.

4. The method as recited in claim 1, wherein the step of complete neutralization occurs before the step of deacetylation.

5. Method according to claim 1 characterized in that the solution viscosity range of the produced SCS is adjustable between 10 and 500 mPas, based on a 1% solution in water.

6. Method according to claim 1 characterized in that the native cellulose is expanded in a polar solvent selected of the group of N,N-dimethylacetamide (DMAc), N-methylpyrrolidone (NMP), dimethylsulfoxide (DMSO) and N,N-dimethylformamide (DMF).

7. Method according to claim 1 characterized in that the swollen cellulose is sulfatized with a sulfating reagent, which is selected from a group consisting of sulfuric acid, amido sulfuric acid, sulfur trioxide, sulfuryl chloride and chlorosulfonic acid.

8. Method according to claim 1 characterized in that the swollen cellulose is acetylated with acetyl chloride or acetic anhydride.

9. Method according to claim 1 characterized in that the swelling is accomplished at temperatures from room temperature up to 150° C.

10. Method according to claim 1 characterized in that the acetylation and the sulfation are accomplished at temperatures from room temperature up to 110° C., in particular 20° to 80° C.

11. Method according to claim 1 characterized in that all starting materials are essentially free from heavy metals including Cd, Pb, Hg, Fe, Ni, Ti, Mn, Zn or Cu, the iron content of the produced SCS is $\leq20$ ppm, and, thus, the total heavy metal content without iron of the produced SCS is $\leq10$ ppm.

12. Sodium cellulose sulfate (SCS) obtainable by the method according to claim 1 characterized in that the solution viscosity range of the produced SCS is adjustable between 10 and 500 mPas based on a 1% solution dissolved in water.

13. Sodium cellulose sulfate (SCS) according to claim 12 characterized in that the produced SCS is free of heavy metals including Cd, Pb, Hg, Fe, Ni, Ti, Mn, Zn or Cu, the iron content of the produced SCS is $\leq20$ ppm and the total heavy metal content of the produced SCS is without iron $\leq10$ ppm.

14. Method for the production of microcapsules characterized by the following method steps:
   a) preparation of 0.5 to 10% aqueous solution from the SCS according to claim 12;
   b) preparation of SCS suspension for an encapsulation process by addition of materials to encapsulate to the aqueous SCS solution and optionally the addition of one or more further substrate, carrier additive, solution, preservative, salt, glycerin or DMSO;
   c) dripping the suspension of b) into a complexation bath; and
   d) complexation of the capsules in the bath containing a cationic polymer in aqueous solution.

15. Method according to claim 14 characterized in that the encapsulated materials are of biological origin and are selected from native or modified cells of humans or animals, native or modified bacteria, native or modified viruses, native or modified yeasts, isolated proteins or protein mixtures, antibodies or antibody fragments, and/or nucleic acid molecules.

16. Method according to claim 14 characterized in that for the dripping the vibration procedure and a frequency in the range from 100 to 4000 Hz is employed.

17. Method according to claim 14 characterized in that the complexation is accomplished in a bath, whereby a polymeric cation is selected from the group of dodecylamine, ethylene diamine, piperazine, methylene blue, arginine, triethyltetramine, poly(allylamine hydrochloride), spermine, poly(diallyldimethyl ammonium chloride) (pDADMAC), poly(vinylbenzyltrimethylammonium chloride) and a mixture of the same.

18. Method according to claim 17 characterized in that the complexation is accomplished in a bath with poly(dimethylallylammonium chloride) (pDADMAC) having an average molecular weight from 10,000 to 500,000 grams per mole.

19. A process of encapsulating biological materials comprising the step of encapsulating biological material within the SCS of claim 12.

20. Microcapsules from SCS according to claim 12.

21. Microcapsules from SCS made in the method according to claim 14.

22. Microcapsules from SCS according to claim 20 characterized in that they have a homogeneous size distribution with an average diameter of 0.1-50 µm, 1-100 µm, 50-250 µm, 50-500 µm, 100-250 µm, 100-500 µm, 250-500 µm, 250-700 µm, 200-1500 µm, 500-1000 µm, 600-800 µm, 700-1500 µm, 1000-2500 µm, 1500-3000 µm, 2500-4000 µm or 3000-5000 µm.

23. A process for treating a patient with a medicament comprising the step of implanting or injecting a patient with a medicament that includes the microcapsules from SCS according to claim 20.

24. Method according to claim 1, wherein the base is sodium hydroxide.

* * * * *